United States Patent [19]

Tsuji et al.

[11] 4,446,239
[45] May 1, 1984

[54] LIGHT SCATTERING IMMUNOASSAY INVOLVING PARTICLES WITH SELECTIVE FREQUENCY BAND APPARATUS

[75] Inventors: Yasuhiro Tsuji; Kiyoshige Wakabayashi, both of Saitama, Japan

[73] Assignee: Chugai Seiyaku Kabushiki Kaisha, Tokyo, Japan

[21] Appl. No.: 368,610

[22] Filed: Apr. 15, 1982

[30] Foreign Application Priority Data

Apr. 24, 1981 [JP] Japan .................... 56-62237

[51] Int. Cl.³ .............. G01N 33/54; G01N 21/49
[52] U.S. Cl. .................... 436/532; 250/574; 356/341; 422/73; 436/517; 436/533; 436/537; 436/805; 436/807; 436/817
[58] Field of Search ........... 435/7; 23/915; 436/517, 436/805, 808, 532, 533, 537, 807, 817; 250/574; 356/341; 422/73

[56] References Cited

U.S. PATENT DOCUMENTS

| | | | |
|---|---|---|---|
| 4,080,264 | 3/1978 | Cohen | 435/7 X |
| 4,174,952 | 11/1979 | Cannell | 23/915 X |
| 4,204,837 | 5/1980 | Sternberg | 356/341 X |
| 4,213,764 | 7/1980 | O'Connor | 435/7 X |
| 4,224,304 | 9/1980 | Sawai | 435/7 X |
| 4,268,171 | 5/1981 | Sternberg | 356/341 X |
| 4,401,387 | 8/1983 | Tokinage | 356/341 |

OTHER PUBLICATIONS

S. B. Dubin et al., Proc. N.A.S., vol. 57, 1164–1171 (1967).
G. K. Von Schulthess et al., Molecular Immunology, 17, 81–92 (1980).

*Primary Examiner*—Sidney Marantz
*Attorney, Agent, or Firm*—Biebel, French & Nauman

[57] ABSTRACT

A technique for measuring the degree of an antigen-antibody reaction by preparing a suspension of insoluble microscopic carrier particles of at least one type carrying an antigen, an antibody or a hapten, forming an agglutination promoting or inhibiting reaction system among the insoluble carrier particles based on an antigen-antibody reaction using the suspension and one or more antigen, antibody or hapten, irradiating the solution of the reaction system with laser light and detecting the light scattered from the reaction system at one or more specific angles, detecting a signal indicative of one or more specific frequency bands from the resulting scatter spectrum, and thenceforth calculating the quantity of antigen, antibody or hapten in a specimen on the basis of the detected signal. The intensity spectrum output of filter 11 for frequency band selection is in the form of a square root and is converted into the original intensity spectrum by means of a squaring circuit 12. The output of the squaring circuit is recorded by a recorder 10.

11 Claims, 12 Drawing Figures

LIGHT SCATTERING IMMUNOASSAY INVOLVING PARTICLES WITH SELECTIVE FREQUENCY BAND APPARATUS

BACKGROUND OF THE INVENTION

This invention relates to a method and apparatus for measuring the degree of an antigen-antibody reaction in order to determine the antigen, antibody or hapten level. More specifically, the invention relates to an immunological quantitative method and apparatus in which use is made of a suspension of insoluble microscopic carrier particles having antigen or antibody molecules bonded thereto, wherein the agglutination reaction among the carrier particles based on the antigen-antibody reaction is measured by optical means. Alternatively, the immunological quantitative method and apparatus to which the invention pertains are adapted to optically measure the degree of a so-called agglutination inhibiting reaction. This is a reaction in which a specimen of interest is introduced, along with an antibody, into a suspension of insoluble microscopic carrier particles having antigenic molecules bonded thereto. The introduced antibody forms bonds with the antigen molecules borne by the carrier particles, causing the aggregation of the carrier particles. Such aggregation is inhibited by the free antigen attributed to the specimen, so that measuring the agglutination inhibiting reaction makes it possible to quantitatively determine the antigen level of the specimen.

The in vitro analysis of substances, beginning with immunological analytical methods which utilize the high degree of specificity between antigens and antibodies, is an important technique essential to modern medical diagnosis and treatment. Radioimmunoassay (RIA) and enzyme immunoassay (EIA) methods are available for the in vitro immunological analysis of small quantities of substances. The RIA method, however, requires special facilities and trained technicians for the handling of radioactive isotopes, and an attendant problem is the treatment of wastes following analysis. In addition, the RIA method is disadvantageous in that it requires the implementation of a complex operation known as B/F separation, in which an antibody with a bonded antigen (or an antigen with a bonded antibody) is separated from a free antibody (or free antigen). The EIA technique does not employ radioactive material, but does generally call for the B/F separation. A homogeneous immunoassay technique does exist in which B/F separation is unnecessary. With this technique the antigen is bonded to an enzyme, and it is required to maintain the antigenic property of the antigen molecules as well as the activity of the enzyme. When the antigen molecules are as massive as protein molecules, however, enzyme activity is difficult to maintain, so there is a restriction upon the kind of antigen molecules to which this method can be applied.

In recent years, various methods based on the quantification of agglutination reactions using an insoluble carrier have been proposed for the purpose of detecting antigen or antibody molecules. Such methods include analysis based on electrical resistance pulses, light scattering and turbidimetry. For example, Philip Blume and Leonard J. Greenberg describe a method based on light scattering (*Clinical Chemistry*, Vol. 21, No. 9, 1975, pp. 1234–1237.). Utilizing the fact that the angular dependence of scattered light intensity varies with the particle size of a particle suspension, the authors find the angular differential (tangential slope) of the scatter intensity at a constant angle and establish a relation between the value found and the concentration of a specimen of interest in order to assay a rheumatoid factor. Latex particles are employed to effect the agglutination reaction. In addition, U.S. Pat. No. 4,174,952 issued to David S. Cannel et al., as well as the periodical Molecular Immunology (Vol. 17, 1980, pp. 81–92), discloses determining the degree of agglutination reactions by measuring the ratio of intensities of light scattered at angles of 90° and 10° with respect to the path of the incident light. According to the disclosed methodology, an agglutination reaction gives rise to an increase in average particle diameter and a simultaneous decrease in the total number of particles. The intensity of light scattered at 90° therefore will decrease as agglutination proceeds, while the scatter intensity at 10° will increase. This permits the ratio of these two intensities to be correlated to the degree of the agglutination reaction. Further, the periodical Immunochemistry (Vol. 12, 1975, pp. 349–351; Vol. 13, 1976, pp. 955–962), as well as U.S. Pat. No. 4,080,264 (issued in 1978), discloses that when a specimen is irradiated with laser light, (a) the scattered light receives a Doppler shift, and has its spectrum line width broadened, owing to the Brownian motion of the insoluble carrier particles, and (b) that it is possible to analyze very small quantities of IgA or human chorionic gonadotropin by finding the diffusion constant of the Brownian motion from the half-value width of the above spectrum. The basic principles involved here are optical mixing spectroscopy or light beating spectroscopy. Light beating spectroscopy provides a high level of sensitivity since detection is possible even at the stage where the carrier particles are in the form of microscopic polymers before growing into large visible or microscopic clumps. In order to analyze the frequency of the output current from the photodetector, however, light beating spectroscopy requires the installation of costly measuring instruments such as a spectrum analyzer or correlator, as well as considerable skill in operation and maintenance.

Figures 1, 2:
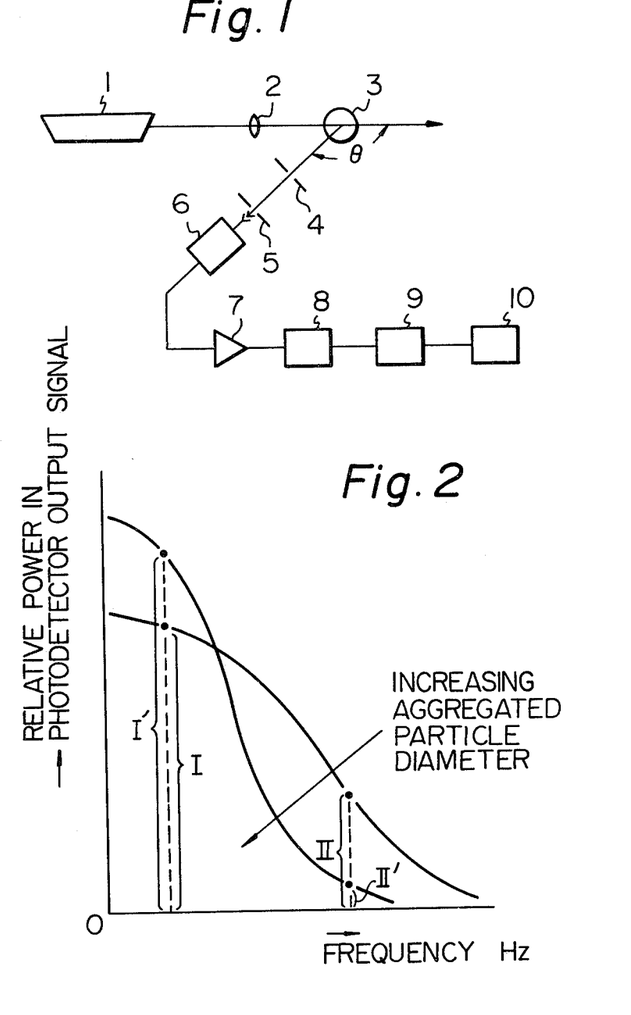
FIG. 1 is an illustrative view showing the basic arrangement of a system for measuring scattered light by light beating spectroscopy according to the prior art.
FIG. 2 is a graph showing change in the frequency spectrum vs. scatter intensity in accordance with agglutination degree.

A basic arrangement for light beating spectroscopy is as shown in FIG. 1. A laser beam of a fixed wavelength emitted by an He-Ne, Ar-ion or other laser 1 is focused by a lens 2 and irradiates a scattering cell 3 containing the specimen of interest. Light scattered through an angle $\theta$ with respect to the optic axis of the laser beam is detected by a photodetector 6, such as a photomultiplier tube, after passing through slits, 4, 5 which determine the field of view. The output signal from the multiplier tube 6 is subjected to a frequency selection operation by a spectrum analyzer 8 after amplification by a preamplifier 7. The signal then is applied to a recorder 10 via a squaring circuit 9 to provide an indication of the frequency spectrum.

Before proceeding further, let us discuss the light scattering phenomenon exhibited by an aggregate of insoluble carrier particles that makes possible the application of the foregoing principle. Monodisperse latex particles suspended in a liquid exhibit Brownian motion. The following well-known formula may be used to express the spectral distribution of scattered light intensity arising from the translational Brownian motion of spherical particles:

$$I(K, \Delta v) \propto \frac{2K^2D}{(\Delta v)^2 + (K^2D)^2} \quad (1)$$

Where
- $\Delta v$: frequency difference between incident and scattered light
- $D$: diffusion constant of particles
- $K$: wave vector given by $$K = \frac{4\pi n_o}{\lambda_o} \sin\frac{\theta}{2}$$

($\mu_o$: wavelength of incident light in vacuum; $n_o$: refractive index of solvent; $\theta$: scatter angle)

For spherical particles, the Stokes-Einstein relation gives us:

$$D = (kBT/3\pi d\eta) \quad (2)$$

where
- kB: Boltzmann constant,
- T: absolute temperature,
- d: particle diameter,
- $\eta$: solvent viscosity coefficient.

Since Eq. (1) may be written $I(K, \Delta v) \propto 2/K^2D$ at the center frequency, namely for $\Delta v = 0$, the beating signal has the form of a Lorentz equation, and the half-value width $\Delta V_{\frac{1}{2}}$ may be written:

$$\Delta v_{\frac{1}{2}} = K^2D \quad (3)$$

for $\Delta v$ satisfying $I(K, \Delta v) = 1/K^2D$. Thus, if we measure the half-value width of the frequency spectrum of the beating signal arising from the scattered light, then the diffusion constant D can be computed since K is determined by the values of $\lambda_o$, $n_o$ and $\theta_o$, which are already known. When aggregation occurs among carrier particles, the aggregate usually is rod-shaped or elliptical rather than spherical owing to the particle alignment or internal structure. Since such aggregates possess rotational freedom, however, the agglutination reaction can be measured quantitatively on the basis of an increase in the diameter of the aggregates. In actual practice, however, not only is the number of monomers (particles) in each aggregate not fixed, but there are also differences in size and a wide variety of alignments, internal structures and particle distributions. A theoretical analysis of the above is attempted in the periodical *Bulletin of Mathmatical Biology* (Vol. 42, pp. 17–36 and 37–56).

In summary, with light beating spectroscopy, the increase in particle diameter due to the agglutination reaction is detected as an average value taken among the aggregates. Thus, factors remain which prevent an improvement in measurement accuracy and sensitivity. One such factor obviously is the distribution of the degree of aggregation, and another is that it is not possible to gain a full understanding of the reaction sytem at the beginning of the agglutination reaction.

BRIEF SUMMARY OF THE INVENTION

The present invention has been developed in view of the foregoing circumstances and seeks to improve the sensitivity and accuracy of quantitative measurement. The underlying principle of the invention, which is based on the analysis of agglutination reactions via light beating spectroscopy, resides in selectively detecting scattered light intensity signals originating from aggregates of all particle diameter ranges formed as a result of agglutination promoting or inhibiting reactions which take place among insoluble carrier particles, and then establishing a correlation between the detected signals and the antigen, antibody and hapten concentration. When the scattered light is photoelectrically converted to provide an output current, the frequency spectrum thereof generally gives a Lorentz curve for the spherical particles, as set forth above. As is apparent from FIG. 2, an increase in the diameter of the aggregated particles mitigates the influence of the solvent molecules and lowers the rate of Brownian motion exhibited by the particles, with a correspondingly smaller frequency difference (Doppler shift) appearing between the light incident upon the scattering cell and the scattered light. In consequence, there is an increase in the proportion of the signal component indicative of the frequency of the irradiating light and, conversely, a decrease in the proportion of the signal component whose frequency is remote from the irradiating light frequency. In FIG. 2, I denotes a scatter output signal from a photodetector in the low-frequency region before particle aggregation proceeds, and I' the same signal after a high degree of aggregation is reached. II represents a scatter output signal in the high-frequency region under a low degree of aggregation, and II' the same signal under a high degree of aggregation. Examining the ratio of the signals reveals that I'/II' gives a value much larger than I/II. In other words, when the frequency difference between the irradiating (incident) laser light and the scattered light is plotted along the horizontal axis and the scattered light intensity for each frequency region is plotted along the vertical axis, and when these are plotted along with particle aggregation, the result is an indication of spectral variation in accordance with a Lorentz curve. In general, when the degree of aggregation is high, the photoelectric output signal or signal intensity is high on the low-frequency side and low on the high-frequency side. Accordingly, if a signal output representative of a specific frequency band, a signal output representative of a reference frequency band, and the ratio of these two outputs are measured, then the degree to which carrier particles aggregate through intervening antigens, antibodies or haptens can be determined, allowing a quantitative correlation to be established between the degree of aggregation and the composition of a specimen of interest, with a high level of accuracy and sensitivity. This will enable keener detection of agglutination degree than was possible with the method of measuring, over the entire frequency range, an intensity spectrum at a certain scatter angle from the light scattering cell, and then finding the mean diffusion constant of the carrier particles from the half-value width of the spectrum.

When detecting the aforementioned scatter output signal of a specific frequency band at a specific scatter angle, a single frequency band or a plurality thereof may be used, with the number being adjusted up or down in accordance with the mode of the agglutination promoting or inhibiting reaction system. Further, the scattered light may be detected at a plurality of scatter angles, and output signals indicative of such scatter may be detected simultaneously. Then, according to the invention, signal intensity is extracted from the signal frequency band or from each of the plural frequency bands, and can be utilized in a prescribed calibration. If the number of frequency bands is increased or the band width broadened, then the magnitude of the scatter output signal can be enlarged to enhance the signal-to-noise ratio. However, care must be taken since too many frequency bands and too broad a bandwidth will destroy the signal singularity and diminish analytical sensitivity and accuracy.

If certain information is known such as the carrier particle characteristic, the type of antigen, antibody or hapten in the specimen, the type of solvent, the incident laser wavelength and the set scatter angle, then it is possible to quantify the agglutination system by finding the power value, corresponding to the scatter intensity, from the photoelectric current, namely the scatter output signal representative of the single frequency band or of each of the plural frequency bands, as mentioned above, or even by measuring the ratio of the total power value of all frequency bands or of a specific frequency band, to a value which may or may not include a Schottky noise component (due to a photoelectric converter) in the power value of each frequency band. Since the scatter output spectrum arising from the Schottky noise will influence the frequency characteristic over the entire bandwidth, the high-frequency band signal or power will include almost no scatter spectrum information in the abovementioned Lorentz curve. Accordingly, if the high-frequency band power is extracted as noise power and is then subtracted from the power value of each specific frequency band, the result will be the essential power. The essential power reflects the scatter spectrum information, namely the agglutination promoting or inhibiting reaction system, with greatly improved accuracy. In such case calculations may be carried out with the width of the high-frequency band from which the noise power is extracted, set equal to the width of each of the other low-frequency bands. Alternatively, when the two band widths involved in the calculation are different, it will be necessary to compute the essential strength (power), or the essential output signal, by calibrating the signal or signal intensity of each specific frequency band based on the ratio of the two bandwidths.

In accordance with the present invention, any microscopic particles which are insoluble in the solution to be analyzed can be utilized as carrier particles. The average particle is 0.1 to 10 microns, preferably 0.2 to 10 micron. Examples of carrier particles which can be used are polymeric latex particles, glass spheres, microscopic oxide powders of alumina, silica-alumina or the like, or biological particles such as coccus-type bacteria, rickettsia, viruses, cell membrane fragments or red blood cells. Examples of antigen which can be analyzed are micro-organisms, tissue antigen including antigen differentiated by particular organs, hormones, enzymes, blood cell antigen and blood-type antigen. An example of the antibody is one which includes an autoantibody. Moreover, it is possible to analyze hapten molecules which, though they can form bonds with antibodies, do not have the capability of inducing an immune response without first being bonded to the carrier before dosing the living body. In the cases described above, the bonding between the insoluble carrier particles and the antibody, antigen or hapten is induced by physical bonding, namely electrostatic attraction, adsorption or hydrophobic bonding, or by chemical bonding due to covalent bonds, using a condensation agent such as carbodimide, a cross-linking agent such as glutaric aldehyde, etc.

Thus the present invention is based on the fact that when an agglutination promoting or agglutination inhibiting reaction exhibited by insoluble carrier particles changes as a function of the quantity of antigen, antibody or hapten in the specimen, the scattered light spectrum will represent the degree of carrier particle agglutination, or the value of a frequency shift peculiar to the distribution of the agglutination degree. The present invention makes use of this fact by measuring the scattered light intensity of a frequency band having a constant shift to compute the degree of agglutination, enabling the antigen, antibody or hapten level to be analyzed with high sensitivity and accuracy. Moreover, the invention makes it possible to actually measure, in a technically simple and inexpensive manner, the scatter spectrum intensity component of a specific frequency band corresponding to the abovesaid frequency shift. This may be achieved by incorporating an electrical filter in a system for processing the signals indicative of the received light, which filter will be designed to set the pass band in accordance with the kind of insoluble carrier particles and the type of antigen, antibody or hapten which is the object of analysis. An electrical filter satisfying the above requirement is cheaper and easier to manufacture and operate than the frequency analyzers or correlators ordinarily employed in light beating spectroscopy.

In order to attain the foregoing objects, the present invention provides a technique for measuring the degree of an antigen-antibody reaction by preparing a suspension of insoluble microscopic carrier particles of at least one type carrying an antigen, antibody or hapten, forming an agglutination promoting or inhibiting reaction system among the insoluble carrier particles based on an antigen-antibody reaction using the suspension and one or more antigen, antibody or hapten, irradiating the solution of the reaction system with laser light and detecting the light scattered from the reaction system at one or more specific angles, detecting a signal indicative of one or more specific frequency bands from the resulting scatter spectrum, and thenceforth calculating the quantity of antigen, antibody or hapten in a specimen on the basis of the detected signal. Further, the present invention provides a technique for measuring the degree of an antigen-antibody reaction by detecting scatter spectra at a plurality of specific scatter angles and detecting the respective signals representative of specific frequency bands for these spectra to compute the ratios of the signals, or by detecting signals from a plurality of frequency bands for a scatter spectrum obtained at a specific scatter angle, namely from both bands of low- and high-frequency (of which the latter or high-frequency band possesses little scatter information) to find either the ratio of the low-frequency band component to the high-frequency band component, or the essential signal magnitude by subtracting the high-frequency component from the low-frequency component before computing the ratio.

Other features and advantages of the invention will be apparent from the following description taken in conjunction with the accompanying drawings in which like reference characters designate the same or similar parts throughout the figures thereof.

DESCRIPTION OF THE PREFERRED EMBODIMENT

Figure 3:
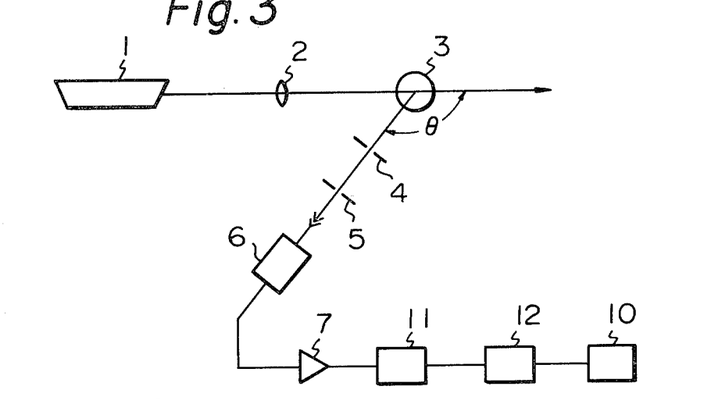
FIG. 3 is a basic block diagram showing a fundamental arrangement according to the present invention.

FIG. 3 shows the basic arrangement of a system, which includes a single filter, for measuring the degree of an agglutination promoting or inhibiting reaction based on light beating spectroscopy. Numerals 1 through 7 denote the similarly labeled components already described in connection with FIG. 1. In FIG. 3, the signal from the preamplifier 7 is applied to a filter 11 for frequency band selection. The intensity spectrum output of the filter 11, which exits from the filter in the form of a square root, is converted back into the original intensity spectrum by means of a squaring circuit 12, whose output is recorded by the recorder 10. The optical system and the light scattering cell 3 are set so that the scattered light is received at an angle $\theta$ with respect to the incident laser beam. The scatter angle is freely adjustable.

Figure 4:
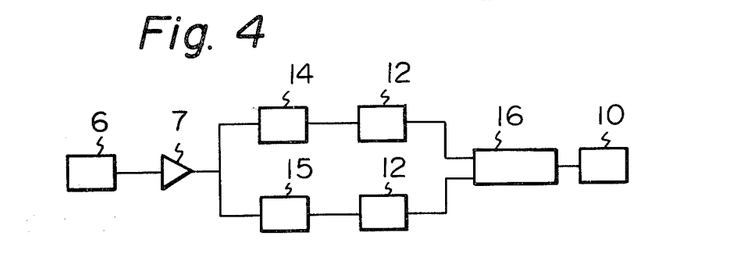
FIGS. 4 through 7 are circuit block diagrams showing examples of processing circuits for detected scatter spectrum signals.

The arrangement shown in FIG. 4 is provided with two filter systems based on filters 14, 15 each of which receives the output of the photodetector 6 following amplification by amplifier 7. Each filter is adapted to select an intensity spectrum of a different frequency band. Each resulting spectrum signal is squared by the squaring circuit 12 and then applied to a divider 16 which finds the intensity ratio of one band to the other (namely the ratio of the corresponding photoelectrically converted power values). The result is recorded by the recorder 10.

Figure 5:
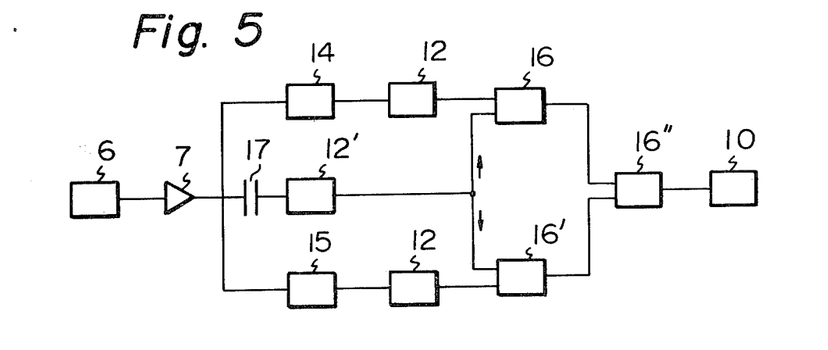

FIG. 5 shows another arrangement which, besides selecting the power values of two different frequency bands by means of the two filters 14, 15 and squaring circuits 12 following amplification of the photodetector output by the amplifier 7, is further provided with a capacitor 17 and a squaring circuit 12' which process the amplified photodetector output to detect the AC component of the scatter intensity spectrum. The divider 16 and an additional divider 16' compute the ratio of the overall AC component to the passed component of each frequency band, after which a multiplier 16" takes the product of the two divider outputs and applies the result to the recorder 10, whereby the degree of agglutination can be measured.

Figure 6:
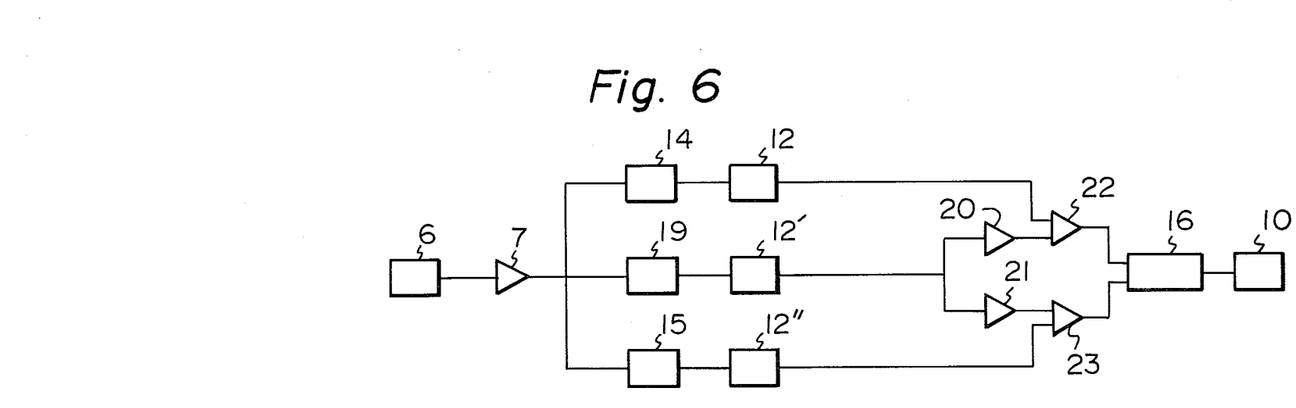

In FIG. 6, the photodetector 6 which receives the scattered light from the scattering cell has its output amplified by the amplifier 7, as before. Now, however, the amplified output is discriminated as three scatter intensity signals of three respective bandwidths by three filters 14, 15, 19. The filters 14, 15 extract two different low-frequency band components to pick out the power components of each frequency band, namely signals related to the two scatter spectrum intensities, and the filter 19 extracts the high-frequency band component as noise power. The output of filter 19 is converted back into an intensity signal by the squaring circuit 12' and then applied to amplifiers 20, 21 for frequency band calibration. Here calibration is so effected as to establish equivalence between the high-frequency bandwidth extracted as the noise power and each of the low-frequency bandwidths. The noise power of this high-frequency band then is subtracted from the scatter intensity signals of the two low-frequency bands by means of subtraction circuits 22, 23, the results of the subtraction operations being applied to the divider 16. When the divider 16 finds the ratio of the two low-frequency band outputs, the result is actually the ratio of the essential low-frequency power values. This arrangement makes it possible to detect even minute changes in agglutination degree with a high sensitivity and accuracy.

Figure 7:
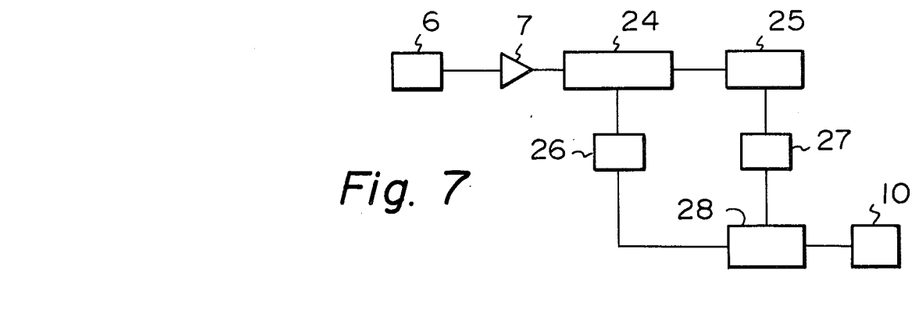

FIG. 7 illustrates a circuit arrangement which facilitates signal processing after the ampifier 7 amplifies the output of the photodetector 6. To this end the arrangement is provided with a programmable switch capacitor filter 24, an AD converter 25, interfaces 26, 27, and a microcomputer 28. According to this arrangement, when it is required the microcomputer 28 sets the programmable filter 24 to a frequency band specified in advance by a program. This enables scatter outputs corresponding to a plurality of frequency bands to be measured successively, and permits various arithmetic operations among these measured values to be specified at will. An additional advantage is that in programming frequency selection, it is possible to vary the pass band of the scatter spectrum signal with facility in accordance with the type of antigen-antibody reaction, the measurement conditions, reagent composition and carrier particle diameter.

Figures 8, 9:
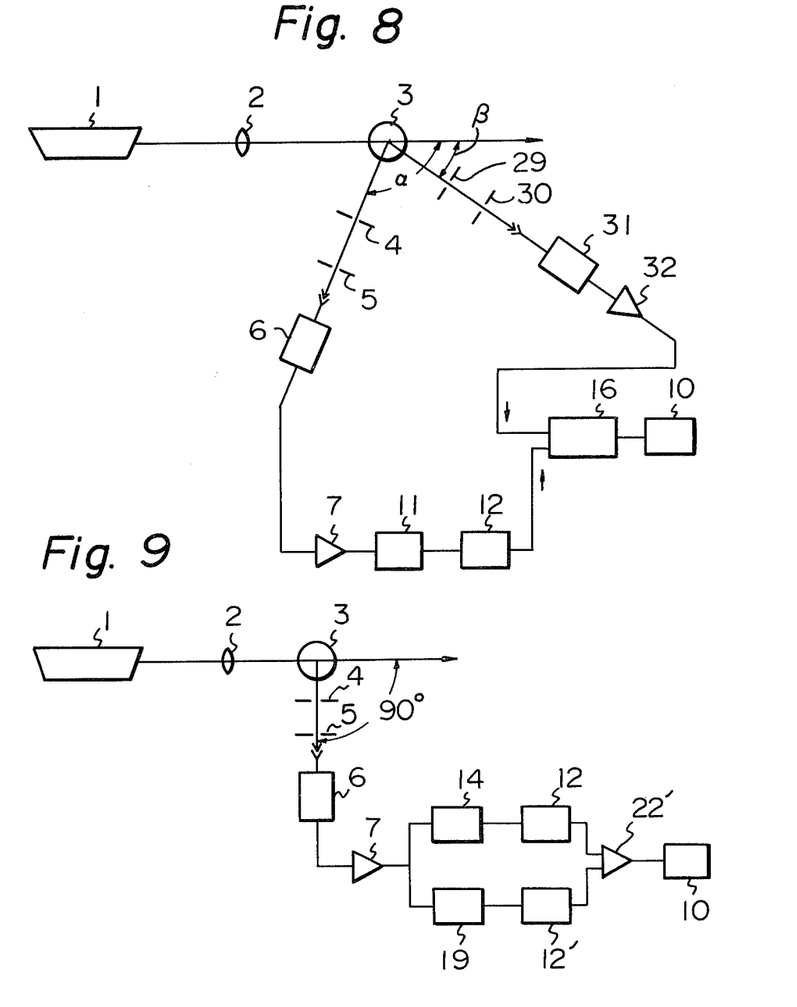
FIG. 8 is an illustrative view showing the basic arrangement of a system for measuring the degree of agglutination in an antigen-antibody reaction system by adopting two scatter detection angles and computing the ratio of a spectrum signal, indicative of a specific frequency band, obtained at one of the detection angles, to the spectrum signal, indicative essentially of all frequency bands, obtained at the other detection angle.
FIG. 9 is an illustrative view showing the basic arrangement of a system for observing a reaction system in which agglutination has progressed to a sufficient degree, the scatter angle being set to 90°.

FIG. 8 shows another arrangement in which scattered light from the cell 3 is detected at two scatter angles $\alpha$, $\beta$ by respective photodetectors 6, 31 after passage through corresponding slits 4, 5 and 29, 30 for limiting the field of view. Light scattered along angle $\beta$ travels close to the optical axis of the incident laser beam. According to this arrangement, the optical response of the agglutination system is measured with far greater precision by detecting the scatter intensity at scatter angle $\beta$ to provide scatter information on the agglutination system over all frequency bands, and then by computing the ratio of the spectrum intensity for a specific frequency band at the scatter angle $\alpha$, to the aforementioned intensity. More specifically, the output of the photodetector 31 is amplified by a preamplifier 32 and applied to the divider 16 where it will serve as the denominator in the computed ratio. The other input to the divider 16 is the signal extracted by the filter 11 for passing the specific frequency band and converted back into the intensity signal by the squaring circuit 12. This signal will serve as the numerator. The divider 16 thus computes the ratio between these inputs and applies the result to the recorder 10 as agglutination system data.

In FIG. 9, the scattered light from the cell 3 is detected at a fixed angle of 90°. The photodetector output, following amplification in amplifier 7, is extracted as scatter spectrum information by a low-pass filter 14, squared by the squaring circuit 12 and delivered to an operational amplifier 22' which has a multiplying function. Meanwhile, the photoelectric output also is applied to a band-pass filter 19 whose bandwidth has a lower limit close to the upper band-width limit of the low-pass filter 14. Band-pass filter 19 isolates the power of its photoelectric signal input and applies it to the squaring circuit 12' for conversion back into the light intensity signal. This signal also is fed into the operational amplifier 22 where it is multiplied by the scatter intensity signal of the low-frequency band. The product is coupled to the recorder 10. When the agglutination in the agglutination system progresses to a sufficient degree, the signal which indicates the scatter spectrum of the low-frequency band intensifies while the high-frequency band signal grows weaker. Therefore, by multiplying these two signals as in the above arrangement, the variation in the scatter spectrum can be extracted in more augmented form, enabling keener observation of the agglutination system through a simple set-up.

It should be noted that while a laser beam is employed as the energy for irradiating the light scattering cell 3 in the foregoing arrangements, it is also possible to utilize other electromagnetic waves or even sonic waves if appropriate sonic wave detection circuitry is provided, with the selection being made based on the requirements of the system to be observed.

The following example illustrates the present invention and is not intended to limit the same.

EXAMPLE

Figure 10:
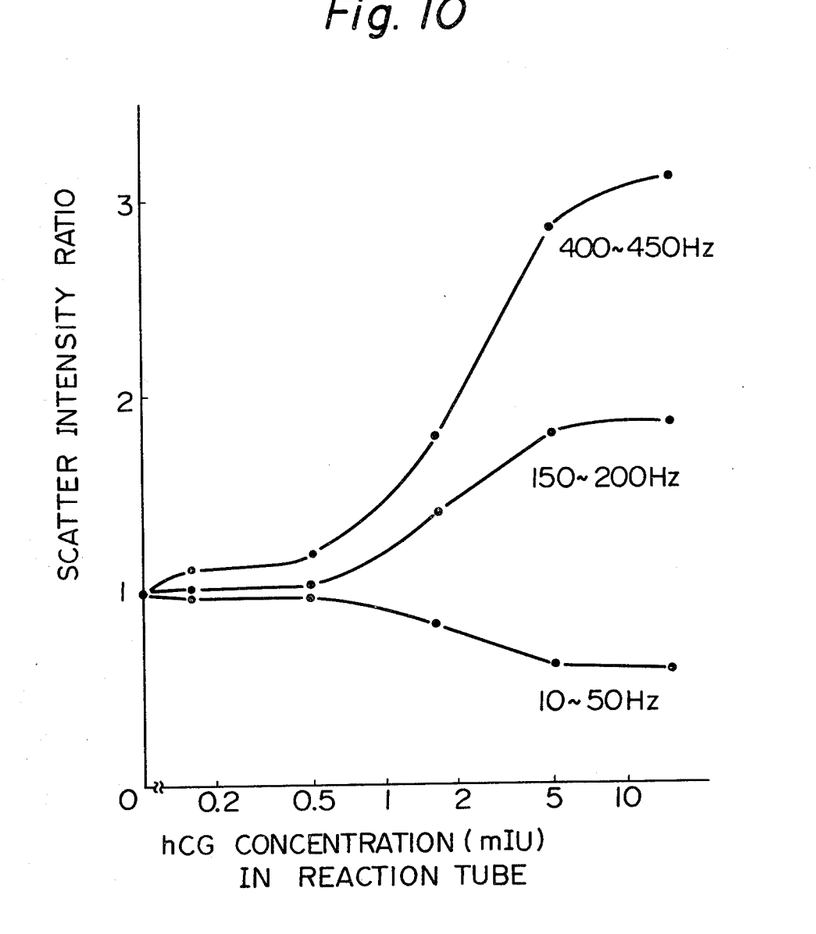
FIGS. 10 through 12 are calibration curves based on data obtained from experiments conducted using the method and apparatus of the present invention.
Figure 11:
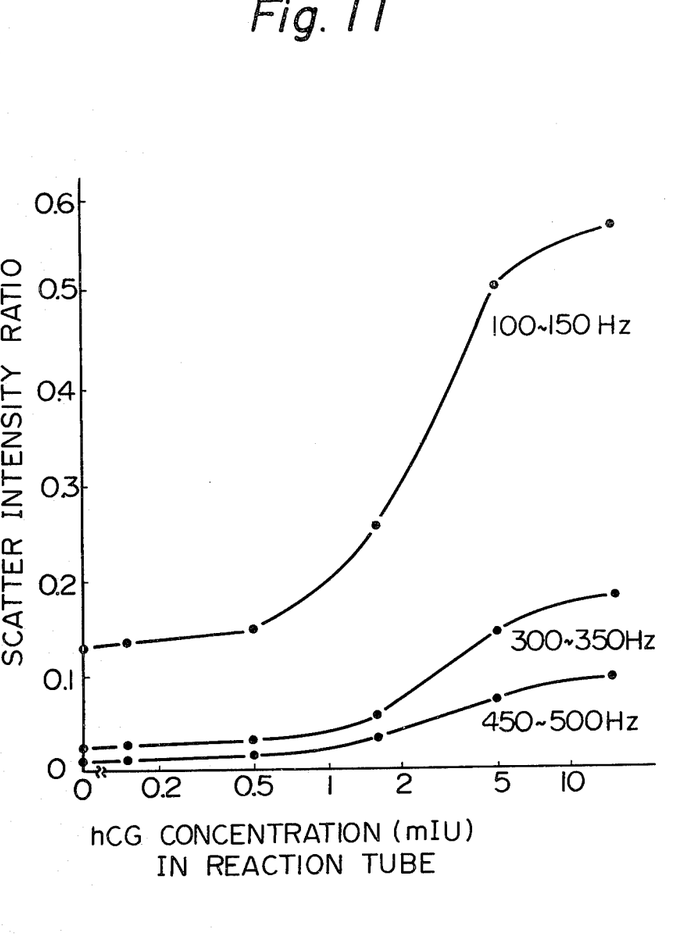

Polybead carboxylate monodisperse microspheres (0.20 μm average diameter) obtained from Polyscience Company (USA) were used as the carrier particles. Human chorionic gonadotropin hCG was bonded to the carrier particles with 1-ethyl-3-(3-dimethyl aminopropyl) carbodiimide serving as the condensation agent. The concentration of the latex particles was adjusted to 200 μg/ml by dilution in 0.15 mol/l pH 8.0 trishydrochloric acid buffer, thereto to prepare a latex suspension reagent. Goat antiserum hCG was diluted 1000 times with the above buffer solution to prepare an antibody solution. Further, the buffer solution was used to prepare a series of hCG standard solutions having concentrations of 0, 1.5, 5, 15, 50 and 150 mIU/ml. Next, 100 μl of each of these hCG standard solutions was taken in a small test tube, to each of which 0.1 ml of the above antibody solution was added. After reacting each mixture at 25° C. for 60 min., 0.1 ml of the above latex solution was added and each mixture was reacted for another 3 hrs. Next, 1 ml of the above buffer solution was added to each reactant solution, and light scattering measurements were performed using a linearly polarized helium-neon laser run at 5 mW output with an oscillating wavelength of 633 nm to irradiate the light scattering cell. The adopted scatter angle was 90°, using the scattered light photometry and signal processing system of FIG. 4. In conducting the measurements, band-pass filter 14 was varied over three pass bands (10–50 Hz, 150–200 Hz, 400–450 Hz), while filter 15 was set to a single pass band of 10–10000 Hz. The ratio of the scatter spectrum intensity of each of the three pass bands to that of the single wide pass band was detected as described above in connection with FIG. 4. The ratios determined were plotted along the vertical axis, and the hCG concentration in the reaction tube (the light scattering cell) was plotted along the horizontal axis. The result is shown in FIG. 10. A further series of measurements were taken with the filter 15 held at a constant pass band of 10–50 Hz and the filter 14 varied over three pass bands (100–150 Hz, 300–350 Hz, 450–500 Hz, each pass band having a bandwidth of 50 Hz). The intensity ratios of the spectrum signal for the former pass band (10–50 Hz) to that for each of the latter three pass bands, were plotted as calibration curves, giving the results shown in FIG. 11.

Figure 12:
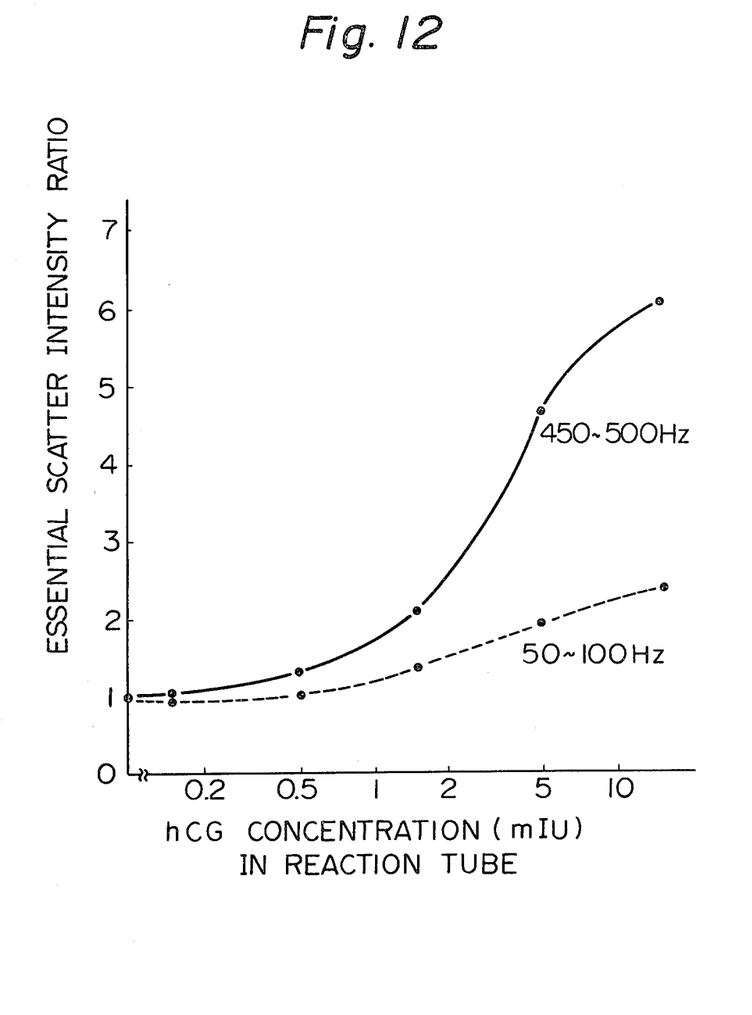

The arrangement of FIG. 9 was employed in the same manner to plot calibration curves, shown in FIG. 12, by extracting the power of a 950–1000 Hz band through the highpass filter 19 and the scatter spectra of two frequency bands (50–100 Hz, 450–500 Hz) through the filter 14. In this case, both of the filters 14, 19 have a bandwidth of 50 Hz. It may be understood, therefore, that the amplifiers 20, 21, of the type shown in FIG. 6 for bandwidth calibration, are unnecessary.

As many apparently widely different embodiments of the present invention can be made without departing from the spirit and scope thereof, it is to be understood that the invention is not limited to the specific embodiments thereof except as defined in the appended claims.

What is claimed is:

1. A method of measuring an antigen-antibody reaction comprising the steps of:
    preparing a suspension of insoluble microscopic carrier particles which carry at least an antigen, an antibody or a hapten;
    forming an agglutination promoting or agglutination inhibiting reaction system among said carrier particles based on an antigen-antibody reaction, using said suspension and one or more antigen, antibody or hapten;
    irradiating said agglutination promoting or agglutination inhibiting reaction system with light having a limited frequency bandwidth;
    detecting light scattered at one or more specific angles from said reaction system;
    selecting signals representative of one or more specific frequency bands from a spectrum signal representative of said scattered light, said specific frequency bands comprising limited frequency portions of the entire bandwidth of said spectrum signal; and
    analyzing the antigen, antibody or hapten in a specimen of interest based on one or more of said selected signals.

2. A method of measuring an antigen-antibody reaction according to claim 1, further comprising the step of measuring the quantity of said antigen, antibody or hapten by detecting scatter intensity spectra at two of said specific angles and computing the ratio between the selected signals representative of said specific frequency bands.

3. A method of measuring an antigen-antibody reaction according to claim 1 or claim 2, further comprising the step of computing the ratio between scatter spectrum intensity signals of two of said specific frequency bands upon detecting a scatter intensity spectrum at one of said specific angles, in order to measure the quantity of antigen, antibody or hapten in the specimen.

4. A method of measuring an antigen-antibody reaction according to claim 3, further comprising the steps of:

detecting light scattered at two or more specific angles from said agglutination promoting or agglutination inhibiting reaction system;

measuring intensity signals of specific frequency bands from respective ones of the obtained scatter spectrum signals; and computing the ratio between scatter spectrum intensity signals of respective ones of said specific frequency bands, thereby measuring the quantity of antigen, antibody or hapten in the specimen.

5. A method of measuring an antigen-antibody reaction according to claim 4, further comprising the steps of:

separating each scatter spectrum output at respective ones of said specific scatter angles into a high-frequency band component which possesses little scatter spectrum information and a low-frequency band component which possesses much scatter spectrum information, and subtracting said high-frequency band component from each of said low-frequency band components, and computing the ratio of the intensities of the resulting low-frequency band components, thereby measuring the quantity of antigen, antibody or hapten in the specimen.

6. An apparatus for measuring an antigen-antibody reaction to determine the quantity of antigen, antibody or hapten in a specimen, which apparatus comprises:

a light scattering cell for receiving a suspension of insoluble microscopic carrier particles which carry at least an antigen, an antibody or a hapten, and a specimen solution which includes at least an antigen, an antibody or a hapten for inducing an antigen-antibody reaction with said suspension;

optical means for irradiating said scattering cell with light having a limited frequency bandwidth;

photodetection means for receiving light, scattered from said cell, at one or more scatter angles and for generating an electrical output signal in response to said light;

selection means for generating scatter spectrum intensity signals representative of one or more specific frequency bands of the electrical output signals of said photodetection means, said specific frequency bands comprising limited frequency portions of the entire bandwidth of said electrical output signals; and indicating means for providing an indication of said scatter spectrum intensity signals.

7. An apparatus for measuring an antigen-antibody reaction according to claim 6, in which said selection means comprises a band-pass filter.

8. An apparatus for measuring an antigen-antibody reaction according to claim 7, in which said band-pass filter comprises a programmable filter.

9. An apparatus for measuring an antigen-antibody reaction according to claim 6, further comprising means for measuring the ratio of said scatter spectrum intensity signal of the specific frequency band to a scatter spectrum intensity signal of virtually all frequency bands.

10. An apparatus for measuring an antigen-antibody reaction according to claim 9, further including means for measuring the ratio between scatter spectrum intensity signals of two of said specific frequency bands.

11. An apparatus for measuring an antigen-antibody reaction according to claim 6 or claim 7 wherein said selection means comprises means for detecting a noise signal.

* * * * *